United States Patent [19]
Fischer et al.

[11] Patent Number: 5,352,190
[45] Date of Patent: Oct. 4, 1994

[54] KNEE BRACE

[75] Inventors: Mark F. Fischer, Colorado Springs; Tammy C. Luttrell, Elbert; Christopher J. Barton, Colorado Springs, all of Colo.

[73] Assignee: Q-Motus, Inc., Colorado Springs, Colo.

[21] Appl. No.: 841,625

[22] Filed: Feb. 26, 1992

Related U.S. Application Data

[63] Continuation-in-part of Ser. No. 495,044, Mar. 16, 1990, Pat. No. 5,117,814, and a continuation-in-part of Ser. No. 507,212, Apr. 9, 1990, Pat. No. 5,178,137, and a continuation-in-part of Ser. No. 550,256, Jul. 9, 1990, Pat. No. 5,144,943.

[51] Int. Cl.[5] .................................................. A01F 5/00
[52] U.S. Cl. ........................................ 602/26; 602/23; 602/20
[58] Field of Search ............ 602/20, 23, 26, 16; 623/39, 20; 2/22

[56] References Cited

U.S. PATENT DOCUMENTS

| 4,256,097 | 3/1981 | Willis | 602/26 X |
| 5,018,514 | 5/1991 | Grood et al. | 623/39 X |

Primary Examiner—Richard J. Apley
Assistant Examiner—Beverly A. Meindl
Attorney, Agent, or Firm—Beaton & Swanson

[57] ABSTRACT

An apparatus for use in bracing or exercising a knee joint in a manner that allows bending of the joint only along a predetermined path which approximates the natural bending of the joint. On one side of the joint are upper and lower struts that run along and are attached to the upper and lower leg and are attached to one another near the joint by a connecting mechanism which includes a set of linkage arms and telescoping elements that allow the struts to pivot relative to one another along the prescribed pivot line. On the other side of the joint are other upper and lower struts that run along and are attached to the upper and lower leg and are attached to one another near the joint by a ball and socket connector. The apparatus may be used as a brace or, alternatively, may be used with a cycling mechanism to cyclically flex and extend the joint or with a force-applying mechanism to apply a constant force urging the extension or flexing of the joint.

11 Claims, 4 Drawing Sheets

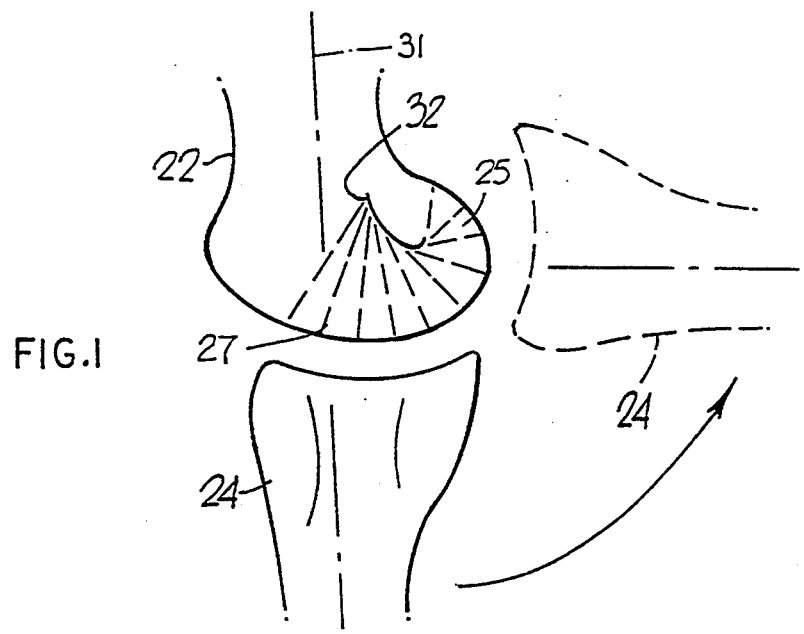
FIG.1
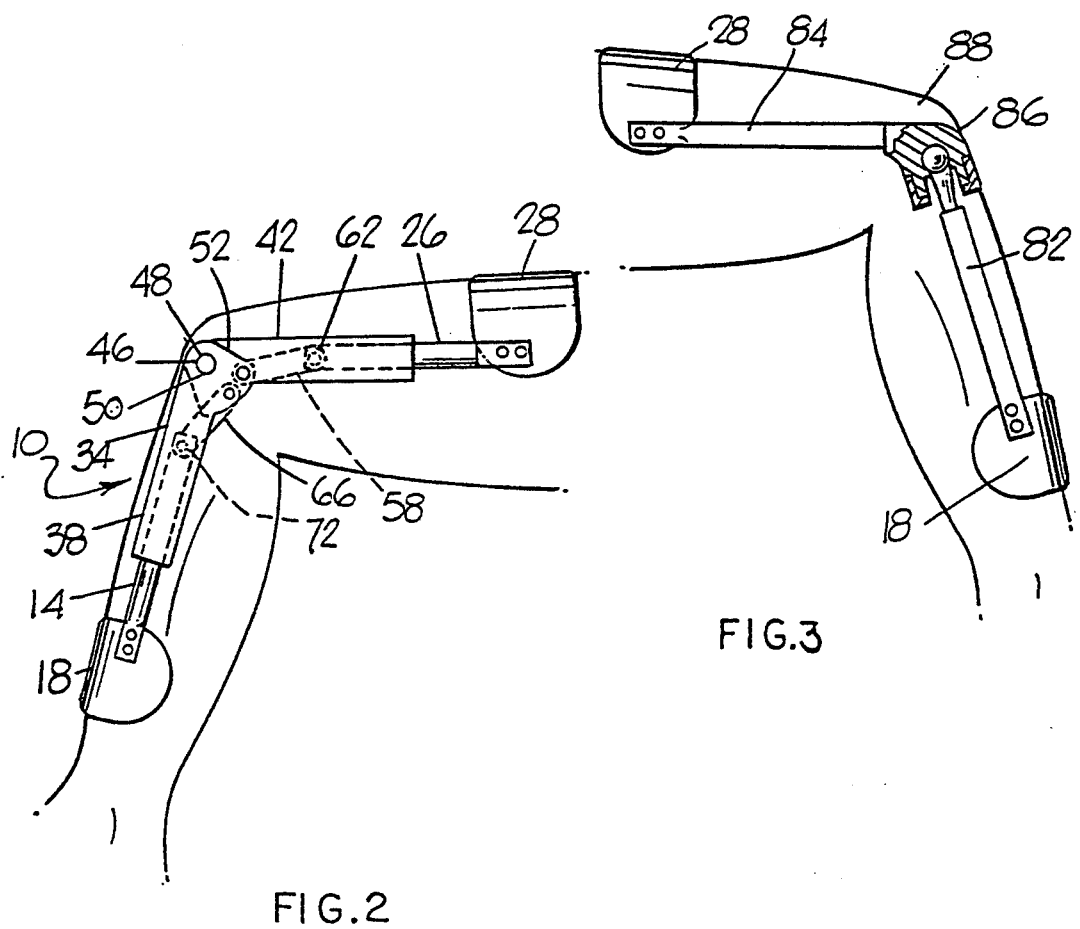
FIG.2
FIG.3

KNEE BRACE

This application is a continuation-in-part of application Ser. Nos. 07/495,044 filed Mar. 16, 1990, now U.S. Pat. No. 5,117,814, Ser. No. 07/507,212 filed Apr. 9, 1990, now U.S. Pat. No. 5,178,137, and Ser. No. 07/550,256 filed Jul. 9, 1990, now U.S. Pat. No. 5,144,943.

BACKGROUND OF THE INVENTION

A loss of joint flexibility is experienced by individuals recovering from neuromuscular diseases, joint replacements, burns, and traumatic injuries such as bone fractures and tendon and ligament tears. In order to regain joint flexibility, it is helpful to flex or extend the joint in a repeated, controlled and quantifiable manner. It is also sometimes necessary to apply a relatively small force of a long duration or repeatedly.

Other individuals require partial immobilization to protect a traumatized joint. The partial immobilization ideally would allow the joint to move through a predetermined range of motion that is necessary for limited locomotion but not through a range of motion that is injurious to the joint, that further traumatizes the joint, or that causes pain to the individual.

The major hinge joints of the limbs, namely the knee and elbow, are particularly difficult to brace and to flex effectively. This is because both the knee and elbow joints have unusual geometries. Rather than merely bending about a pivot axis, the joints are such that the lower limb pivots about a moving axis and also twists slightly. The moving axis effect can be appreciated by reference to FIG. 1, which shows in schematic form the bone structure of the knee joint. The lower femur 22 acts as a ball joint to receive the upper tibia 24. However, the ball of the lower femur is not truly spherical. Instead, it has a radius 25 that is shorter when the joint is bent as compared to a radius 27 when the joint is straightened. In addition, the ball is offset to the rear of the femur relative to the longitudinal axis of the femur. Therefore, the tibia 24 moves away from the longitudinal axis 31 of the femur 22 as the joint bends. This movement of the tibia away from the femur actually lengthens the leg as it bends. A similar process takes place at the elbow.

It can be appreciated from FIG. 1 that the tibia 24 not only moves away from the femur as the joint is bent, thereby increasing the radius of rotation, but also that the axis of rotation moves as the tibia 24 slides down the ball of the femur 22. Again, a similar process takes place at the elbow. The moving axis of rotation describes a curved line 32 which anatomists describe as an "evolute". For purposes of the present patent, an "evolute line" is defined as a curved line having a gradually decreasing radius of curvature along the line.

Another unusual aspect of the bending of a knee or elbow is that as the lower limb straightens relative to the upper limb, it simultaneously rotates along the lower limb axis. The tibia rotates so that the toes turn outward and the heels turn inward as the joint unbends. Conversely, the tibia rotates in the opposite direction as the joint is bent so that the toes turn inward and the heels turn outward. Similarly, at the elbow, the radius and ulna rotate so that the palm turns downward as the elbow is unbent, and the radius and ulna rotate in the opposite directly so that the palm turns upward as the elbow is bent.

It can be appreciated that the combination of an upper limb ball that is offset from the upper limb longitudinal axis, an upper limb ball that is nonspherical, and a twisting action of the lower limb as it bends in relation to the upper limb, results in a complex movement. This complex movement has proven to be difficult to match in devices designed to brace or cyclically flex the joint.

Typical of the prior art are U.S. Pat. Nos. 4,508,111; 4,397,308; 4,485,808 and 4,538,600, all by Hepburn. These devices are designed to cyclically flex the joint. They generally comprise upper and lower struts which attach to the limbs of the desired joint using an appropriate attachment means. The upper and lower struts are pivotally attached to one another at the ends adjacent the joint. The pivotal attachment includes a cylindrical housing with a cam, wherein one of the struts is attached to the cam and the other bears on the cam surface through a bearing spring. Flexing or extending the joint causes a corresponding approximation or alignment of the struts relative to one another and a compression or expansion of the spring. The use of the spring allows a somewhat quantifiable and adjustable constant force to be applied to urge the flexing or extending of the joint. It can be appreciated that the devices in the Hepburn patents make no attempt to match the curved evolute line defined by the bending joint or to account for the rotation of the lower limb about its longitudinal axis as the joint bends.

Other prior art devices are in U.S. Pat. Nos. 4,489,718 by Martin; 4,372,298 by Lerman; 4,361,142 by Lewis; 4,487,200 by Feanny; and 4,686,969 by Scott. As in the devices described in the Hepburn patents mentioned above, these devices do not provide for the range of movement provided for in the present device. In addition, they generally do not include a mechanism to cyclically flex and extend the joint by application of a force in the manner of the dynamic splint embodiment of the present invention and as further described in U.S. application Ser. No. 07/495,044, of which the present is a continuation-in-part.

SUMMARY OF THE INVENTION

The present invention is a device for bracing or for cyclically flexing and extending a joint such as a knee or elbow joint. The device is configured to accommodate the bending of a lower limb about a moving axis that describes an evolute line. It also is configured to allow the lower limb to twist—that is, to rotate about its longitudinal axis—as the lower limb bends relative to the upper limb.

The invention includes an upper strut for attachment to an upper limb, a lower strut for attachment to a lower limb, and a linking mechanism for attachment of the upper strut to the lower strut. The linking mechanism allows the pivoting between the upper strut and the lower strut to describe an evolute line to approximate the evolute line described by the bending of the lower limb relative to the upper limb.

The linkage producing the evolute line may be on both sides of the brace or may be on only the inside of the brace and not on the outside of the brace. In place of the linkage on the outside of the brace, there may be a ball and socket or other suitable connector that does not pivot along the evolute line. In this manner, the rotation axis of the lower strut in relation to the upper strut becomes skewed as the lower limb bends, thereby accommodating the natural twisting of the lower limb about its longitudinal axis as that bending occurs. In an alternative embodiment, the linkage may be on both the inside and outside of the brace, and the natural twisting of the lower limb is accommodated by a pin and slot arrangement connecting the lower strut to the lower limbs through an attachment mechanism.

The linkage between the upper and lower struts in a preferred embodiment includes an upper telescoping portion that telescopes into the upper strut and a lower telescoping portion that telescopes into the lower strut. The two telescoping portions are pivotally attached to one another at a pivot point. The lower strut is pivotally attached to the upper telescoping portion through a linkage arm connected at one end to the top of the lower strut and at the other end to a flange of the upper telescoping portion at a location between the joint and the pivotal attachment of the two telescoping portions. Similarly, the upper strut is pivotally attached to the lower telescoping portion through another linkage arm connected at one end to the bottom of the upper strut and at the other end to a flange of the lower telescoping portion at a location between the joint and the pivotal attachment of the two telescoping portions. The bending of the lower strut relative to the upper strut causes the two linkage arms to drive the struts out of the telescoping portions, thereby effectively lengthening the overall mechanism and describing an evolute line about which the lower strut rotates relative to the upper strut.

The invention can be used as a brace to limit the movement in the joint. As a brace, the invention serves to protect an injured or weakened joint against further injury or weakening by requiring the joint to bend only in the predetermined manner corresponding to the natural uninjured bending of the joint. Alternatively, the invention can be used in combination with a driving mechanism to cyclically flex and extend the joint in the same predetermined manner corresponding to the natural bending of the joint, in order to strengthen the joint. As another alternative, the invention can be used in combination with a force-applying mechanism to apply a constant force urging the flexing or extension of the joint.

BRIEF DESCRIPTION OF THE DRAWINGS

FIG. 1 shows a side elevational view of the lower femur and upper tibia bones where they meet at a knee joint, along with the evolute line described by the bending of the joint and a phantom view of the flexed tibia.

FIG. 2 shows a side elevational view of the present invention from inside a knee joint looking outward.

FIG. 3 shows a side elevational view of the invention from outside a knee joint looking inward.

DETAILED DESCRIPTION OF THE INVENTION

Figure 4:
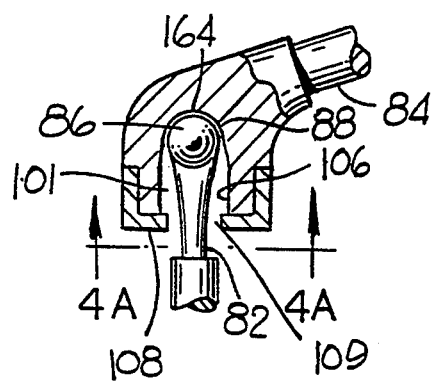
FIG. 4 shows a side sectional view of the ball and socket connection of the invention.

A side elevational view of the invention 10 is shown in FIG. 2, viewed from the inside of the knee looking outward. The invention 10 includes a lower strut 14 which is attached to the lower leg of the patient through a lower cuff 18 which may extend partially or fully around the calf. The invention also includes an upper strut 26 which is attached to the upper leg of the patient through an upper cuff 28 extending partially or fully around the thigh. The cuffs are held in place on the leg by a suitable attachment device such as a strap with an adjustable buckle or VELCRO brand hook and loop fasteners (not shown).

The upper strut 26 and lower strut 14 are connected to one another through a connection mechanism 34. The connection mechanism 34 includes a lower telescoping portion 38 slidably attached to the lower strut 14 and an upper telescoping portion 42 slidably attached to the upper strut 26. The struts 14 and 26 may be cylindrical members and the telescoping portions 38 and 42 may be tubular members, so that the struts and telescoping portions telescope one inside the other. This allows the combined lower strut and lower telescoping portion to lengthen or shorten as they slide along a common longitudinal axis. Similarly, this allows the combined upper strut and upper telescoping portion to lengthen or shorten as they slide along a different common longitudinal axis. The ends of the upper telescoping portion 42 and lower telescoping portion 38 that are nearest to the joint are pivotally connected to one another by a telescoping portion pivot pin 48 extending through holes 46 and 50 in the telescoping portions. The struts and telescoping portions may be of a metal or plastic or other suitable material having adequate strength and capable of being fabricated to the desired dimensions.

Each telescoping portion 38 and 48 has a flange, 52 and 54, respectively, extending roughly perpendicular to the axis of the pivot pin 48 and toward the joint. The upper strut 26 is attached to the lower telescoping portion flange 52 by an upper strut linkage arm 58. One end of the upper strut linkage arm 58 is pivotally attached to the lower end of the upper strut 26 by an upper strut linkage arm upper pivot pin 62 which pivotally extends through the lower end of the upper strut 26 and through the upper end of the upper strut linkage arm 58. The other end of the upper strut linkage arm 58 is pivotally attached to the lower telescoping portion flange 52 by an upper strut linkage arm lower pivot pin 63 which pivotally extends through the lower end of the upper strut linkage arm 58 and the lower telescoping portion of flange 52. Similarly, the lower strut 14 is attached to the upper telescoping portion flange 54 by a lower strut linkage arm 66. One end of the lower strut linkage arm 66 is pivotally attached to the upper end of the lower strut 14 by a lower strut linkage arm lower pivot pin 72 which pivotally extends through the upper end of the lower strut 14 and through the lower end of the lower strut linkage arm 66. The other end of the lower strut linkage arm 66 is pivotally attached to the upper telescoping portion flange 54 by a lower strut linkage arm upper pivot pin 73 which pivotally extends through the upper end of the lower strut linkage arm 66 and the upper telescoping portion flange 54. The flanges may have stops (not shown) that prevent the struts from pivoting too far in one direction to cause hyperextension of the joint. The stops may be adjustable and may stop the rotation in a gradual manner with the use of a cushioning system such as a shock absorber, foam or a spring.

It can be appreciated from the drawings that the two linkage arm pivot pins 63 and 73 that extend through the two telescoping portion flanges 52 and 54, are located in different relative positions on the two telescoping flanges. Both pivot pins are located inside the angle defined by the pivoted upper and lower telescoping portions. However, the upper strut linkage arm lower pivot pin 63 extends through the lower telescoping portion flange 52 at a point that is roughly perpendicular (such as 80° to 100°) to the axis of the upper strut 26 when the joint is unbent, so that the pin moves through an angle of about 0° to 90° as the tibia moves from being bent 90° in relation to the femur to being in-line with the femur, the angle being measured from the telescoping portion pivot 48 and in relation to the axis of the upper strut 26. In contrast, the lower strut linkage arm upper pivot pin 73 extends through the upper telescoping portion flange 54 at a point that is roughly 45° (such as 35° to 55°) from the axis of the upper strut 26 when the joint is unbent. At this position for the pivot pin, the pivot pin undergoes relatively little change in angular position in relation to the upper strut 26 as the joint flexes and extends. It has been found that this positioning of the pivot pins best approximates the evolute line of the bending joint. Of course, other positions may be desirable depending on changes in the structure of the device or use of the device in other applications.

Figure 5:
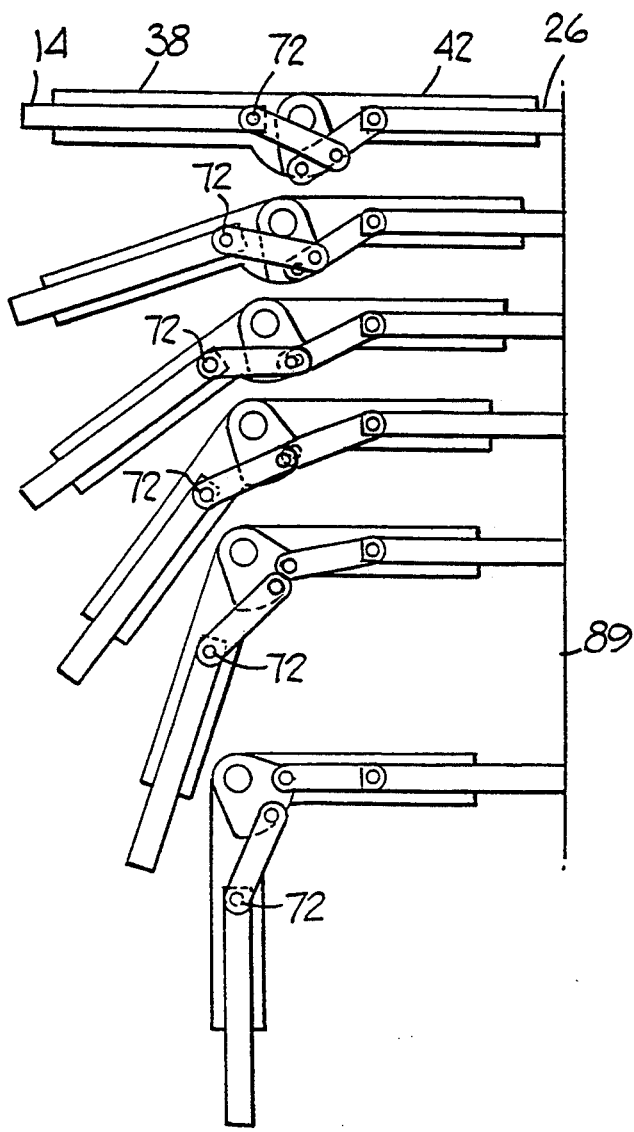
FIG. 5 shows a series of schematic drawings of the linkage of the invention in a preferred embodiment from a side elevational view.

The fact that this connecting mechanism between the upper strut 26 and lower strut 14 enables the struts to move relative to one another in a manner that closely approximates the evolute line described by the tibia as it moves relative to the femur, can be appreciated by the diagrammatic view of FIG. 5. The top drawing of FIG. 5 shows the device in a fully extended position to correspond to a fully extended leg. The lower strut 14 and upper strut 26 are approximately co-axial and the struts 14 and 26 are fully retracted into their respective telescoping portions 38 and 42. The lower drawings of FIG. 5 show the device progressively flexing to correspond to the progressively flexing of a leg. The vertical line 89 to the right of the series of drawings shows a given point on the upper strut 26. Also indicated in the drawings is the lower strut linkage arm pivot pin 72.

This series of drawings demonstrates the movement of the lower strut 14 in relation to the upper strut 26 as the knee gradually bends. One of the components of this movement is the gradual telescoping of the upper and lower struts 26 and 14 out of the upper and lower telescoping portions 42 and 38. This telescoping increases the overall length of the device as measured from the upper cuff 28 to the telescoping portion pivot pin 48 and from the telescoping portion pivot pin 48 to the lower cuff 18. The lengthening of the distance from the upper cuff to the telescoping portion pivot pin 48 is readily apparent by reference to the increasing distance between upper telescoping portion and the vertical line 89 connecting the same point on the upper strut 26 through the series of drawings.

Figure 6:
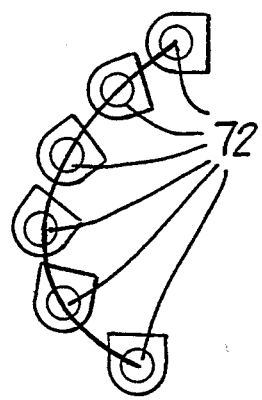
FIG. 6 shows a plot of the path of a point on the device as the device bends through the motion shown in FIG. 5.

Another component of this movement between the upper strut 26 and lower strut 14, which is really an aspect of the lengthening aspect described in the preceding paragraph, is the change in position of the lower strut linkage arm pivot pin 72. That pin is shown in the series of drawings of FIG. 5 and the movement of it is plotted in FIG. 6. It is apparent from these drawings that the pin describes an evolute line closely approximating the evolute line described by the movement of a tibia in relation to a femur or the movement of a radius and ulna in relation to a humerus.

It will be apparent to those skilled in the art that the mechanism described herein for approximating the evolute line described by the movement of a limb joints in relation to one another, it not the only mechanism that will accomplish that purpose. For example, one could perhaps construct other devices that use cams, wedges, pulleys, gears or some other combination of mechanical, electrical or electromechanical elements. The important point is that, whatever the construction, the end product allows the movement between the upper and lower struts to approximate the evolute line describing the movement of the limb joints. It will be apparent to those skilled in the art that, although the invention is described primarily with reference to a knee joint, the same type of arrangement could be used on an elbow where the ulna and radius pivot and turn in relation to the humerus.

The other side of the invention 10, shown from the outside of the knee looking inward, is depicted in FIG. 3. The outside portion of the invention includes an outside lower strut 82 attached to the lower cuff 18 and an outside upper strut 84 attached to the upper cuff 28. In the preferred embodiment, the attachment of the outside lower strut 82 to the outside upper strut 84 is much simpler than the attachment of the lower strut 14 and upper strut 26 on the inside of the invention. Rather than including the telescoping portions included on the inside of the invention which allow the device to flex and extend along the evolute line of the bending knee, the attachment of the outside lower strut 82 and outside upper strut 84 is by a ball and socket. The upper end of the outside lower strut 82 is attached to a ball 86 and the lower end of the outside upper strut 84 is attached to a mating socket 88. The ball 86 and socket 88 mate with one another to thereby attach the outside lower strut 82 to the outside upper strut 84 in a manner that allows universal pivoting of the two struts about the ball and socket. In other words, each strut can move in any manner in relation to the other strut, provided that they remain pivotally connected at the point of the ball and socket.

Figure 4A:
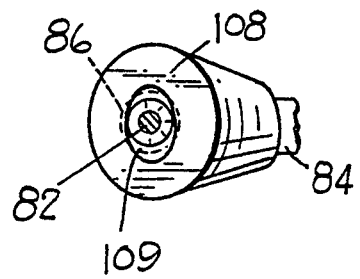
FIG. 4a shows a sectional view, taken along line 4a—4a of FIG. 4 showing the ball and socket connection of the invention.

A side sectional view of the ball and socket arrangement is shown in FIG. 4. The ball 86 is a spherical-shaped enlargement attached to the upper end of the outside lower strut 82. The socket 88 is attached to the lower end of the outside upper strut 84, and includes a void 101 defined by a ball seat 104, a wall 106 and a cap 108. The cap 108 preferably has an opening 109 to receive the upper end of the outside lower strut 82, as better shown in FIG. 4a. The opening 109 is oval shaped, with the long dimension of the oval in the vertical direction, so that there is a relatively large amount of play of the outside lower strut in the vertical direction and a relatively small amount of play in the horizontal direction. The cap 108 may be attached to the ball seat 104 through threads or an adhesive or other suitable arrangement. To assemble the device, the outside lower strut lower end is inserted through the opening 109 from the upper side of the opening and pushed all the way through the opening until the ball 86 rests against the top of the cap 108. The cap is then attached to the ball seat 104, thereby enclosing the ball 86 in the void 101 of the socket 88 while leaving the outside lower strut 82 free to move up and down considerably and side to side slightly through the opening 109.

Of course, it will be apparent to those skilled in the art that the ball and socket could be reversed so that the ball 86 is attached to the outside upper strut 84 and the socket 88 is attached to the outside lower strut 84. Also, universal movement between the outside upper and outside lower struts could be accomplished in ways other than through a ball and socket.

In operation, it can be appreciated that the device approximately matches the alignment of an extended joint. In that condition, the upper and lower struts 26 and 14 are retracted into the upper and lower telescoping portions 42 and 38 and the upper strut 26 is parallel to the lower strut 14. As the joint is flexed so that the tibia bends relative to the femur, the tibia slides over the eccentric ball of the femur to describe an evolute line. The corresponding movement of the lower strut 14 relative to the upper strut 26 on the inside of the device approximates this evolute line, as the upper and lower struts are driven out of the upper and lower telescoping portions 42 and 38 by the upper strut linkage arm 58 and the lower strut linkage arm 66.

At the same time, the outside of the device is restrained by the ball and socket so that there is no evolute movement of the outside lower strut 82 relative to the outside upper strut 84. The tracing of an evolute line by the lower strut 14 in relation to the upper strut 28 while no evolute line is traced by the movement of the outside lower strut 82 relative to the outside upper strut 84, causes a skewing of the axis of rotation. This accommodates the natural tendency of the tibia to twist as the joint bends to cause the toe to turn inward. The play in the ball 86 and socket 88 on the outer side of the device accommodates this twisting of the tibia and skewing of the axis of rotation by allowing a corresponding twisting of the outside lower strut 82.

The discussion above describes the use of the invention 10 as a brace, that is, a device to limit the movement of a joint to a predetermined range. Braces are useful in partially immobilizing an injured joint to prevent further injury so that the joint can heal while the patient makes limited use of it. Next described is the use of the invention 10 in combination with devices to apply a continuous force urging the continuous flexing or extension of the joint, or a device to cyclically flex and extend joint.

Figure 7:
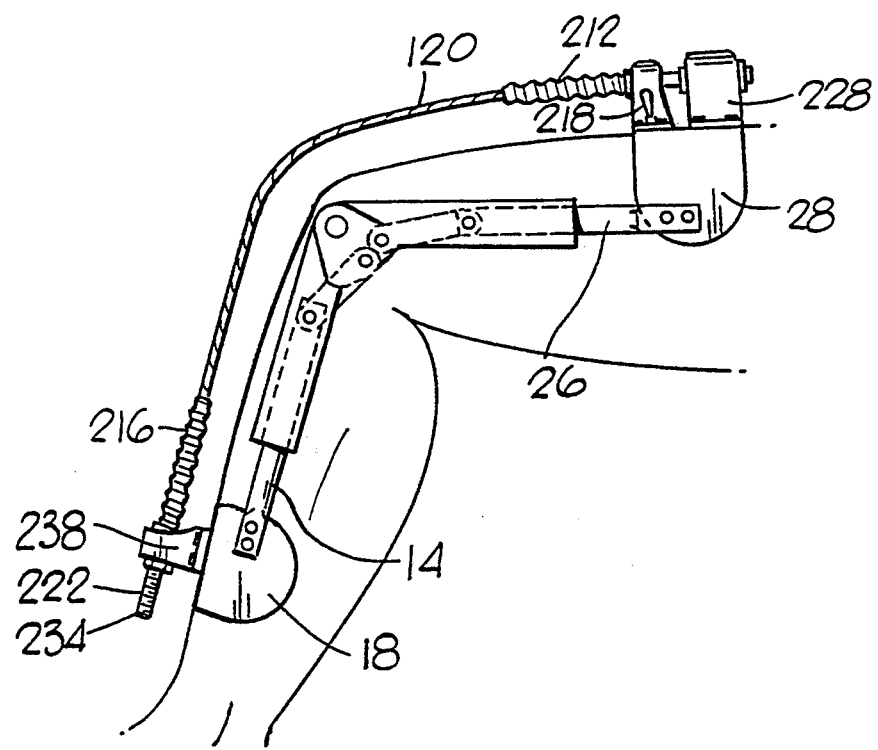
FIG. 7 shows a side elevational view of the present invention from inside a knee joint looking outward in combination with a cycling mechanism to cyclically flex and extend the joint.

FIG. 7 shows a side elevational view of the invention in combination with a cycling mechanism 120, looking from the inside of the brace outward. FIG. 7 does not show the ball and socket connection on the outside of the knee, but it should be appreciated that such connection may be utilized. The cycling mechanism may be substantially the same as the cycling member described in application Ser. No. 07/495,044 of which this is a continuation-in-part and which is hereby incorporated by reference. Briefly, the cycling mechanism includes an extendable cable 212 having a fixed cable sleeve 216 enclosing an inner cable 222 which is rotatably but not slidably mounted in the cable sleeve 216. The inner cable 222 has threads 234 on the lower end which engage mating threads on a lower mounting bracket 238 which is attached to the lower cuff 18. The upper end of the inner cable 222 is attached to a drive means such as a motor 228 which is mounted on the upper cuff 28 and the upper end of the cable sleeve 216 is mounted to the upper cuff 28 through an upper mounting bracket 218.

In operation, the motor 228 is cycled back and forth to repeatedly rotate the inner cable 222 in one direction and then the other. The rotation of the inner cable 228 causes the inner cable threads 234 to thread in and out of the lower mounting bracket 238, thereby shortening and lengthening the distance between the upper mounting bracket 218 and the lower mounting bracket 238. The lengthening of the distance between the brackets causes a bending of the joint along the evolute line described by the connecting mechanism between the upper and lower struts 26 and 14, while a shortening of that distance causes an extension of the joint along that same evolute line. If the apparatus includes the ball and socket connection on the outside of the knee, then the bending of the joint will also accommodate the natural twisting of the tibia.

Figure 8:
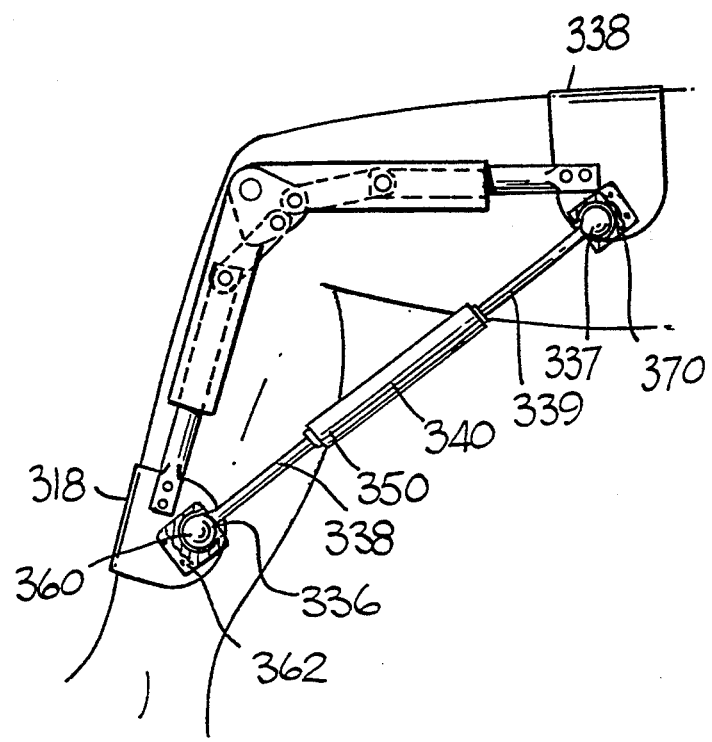
FIG. 8 shows a side elevational view of the present invention from inside a knee joint looking outward in combination with a force-applying mechanism to apply a continuous force urging the flexing or extending of the joint.

Shown in FIG. 8 is the use of the invention in combination with a continuous force-applying mechanism 340 which may be substantially the same as shown in application Ser. No. 07/550,256 of which this is a continuation-in-part and which is hereby incorporated by reference. Briefly, the force-applying mechanism 340 includes an expandable cylinder portion 350 with a lower shaft 338 and an upper shaft 339 that extends from the cylinder portion. The lower end of the lower shaft has a lower shaft ball 336 that mates with a socket 360 in a lower bracket 362 attached to the lower cuff 318. The top of the upper shaft 339 has an upper shaft ball 337 that mates with a socket 370 in an upper bracket 335 attached to the upper cuff 338. The upper shaft 339 can be slid in and out of the cylinder portion 350 to obtain a desired distance between the upper bracket and lower bracket corresponding to a desired degree of bending of the joint. Once appropriate length adjustment are made, a spring (not shown) inside the cylinder portion 50 applies a predetermined adjustable force urging the upper shaft 339 out of or into the cylinder portion 350, thereby urging the flexing or extension of the joint.

Figure 9:
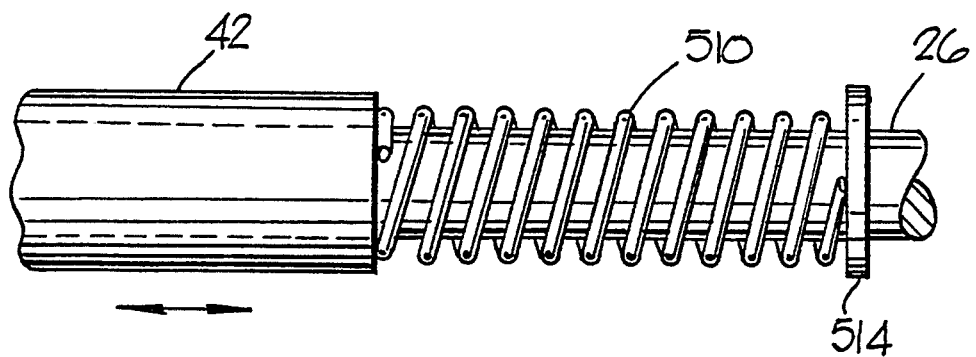
FIG. 9 shows an end elevational view of the slot and pin arrangement for attaching a lower cuff to a lower strut in an alternate embodiment of the invention.

An alternate mechanism for applying a continuous force to the joint is shown in FIG. 9, which shows a detail of the upper portion of the invention where the upper strut 26 meets the upper telescoping portion 42. As shown in FIG. 9, a spring 510 is positioned on the upper strut 26. One end of the spring 510 is attached to or abuts against the upper end of the upper telescoping portion 42 and the other end is attached to or abuts against a stop 514 which is attached to the upper strut 26. In operation, the spring 510 is a compression spring which applies a force urging the upper strut 26 out of the upper telescoping portion 42, thereby lengthening the device to cause the joint to bend. Alternatively, the spring 510 may be a tension spring which applies a force urging the upper strut 26 into the upper telescoping portion 42, thereby shortening the device to cause the joint to unbend. It will be apparent to those skilled in the art that a wide variety of other force-applying mechanisms are possible, both for applying continuous force and for applying cyclical force, such as pneumatic devices and hydraulic devices.

Figure 10:
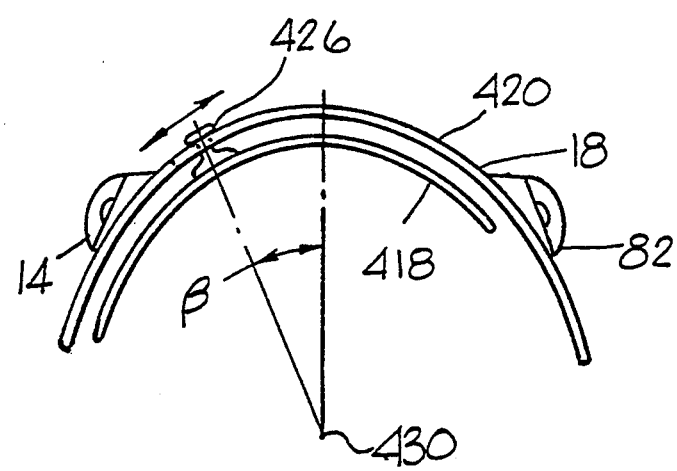
FIG. 10 shows a detail of the upper portion of the invention, showing an arrangement for urging the upper strut into or out of the upper telescoping portion.

An alternate mechanism for accommodating the natural tendency of the lower limb to twist as it bends in relation to the upper limb is shown in FIG. 10. This mechanism may be used with an embodiment of the invention wherein there are linkage mechanisms on both the inside and outside of the limb, rather than a linkage mechanism on one side of the limb and a ball and socket mechanism on the other side of the limb. An advantage to having linkage mechanisms on both sides of the limb rather than having a linkage mechanism on one side and a ball and socket on the other, is that the device is then more rigid and better able to brace the limb against externally induced trauma.

The mechanism as shown in the view of FIG. 10 from the lower limb looking toward the joint, includes the lower strut 14 and the outside lower strut 82 attached to the lower cuff 18. The lower cuff 18 is slidably attached to an inner lower cuff 418 which, in turn, extends partially around and is attached to the lower limb through straps or other suitable means (not shown). As explained previously, the tibia tends to twist so that the toes turn inward as the knee joint bends. Therefore, the end view of FIG. 10 depicts the device on a partially bent left limb such as the left leg. The slidable attachment is accomplished through a slot 420 through the lower cuff 18 which receives a pin 426 attached to the inner lower cuff 418. This slidable attachment allows the inner lower cuff 418 to slide back and forth in relation to the lower cuff 18 in a plane roughly perpendicular to the longitudinal axis of the lower limb. In addition, the curvature of the lower cuff 420 accommodates the twisting of the lower limb by causing the inner lower cuff 418 to rotate slightly in relation to the lower cuff 18 as this sliding takes place. Ideally, this rotation is about the axis of rotation 430 of the lower limb, so that the inner lower cuff 418 moves through an angle $\beta$ from the unrotated position to the rotated position.

Of course, the pin and slot arrangement described above would be reversed. In other words, the slot could be in the inner lower cuff 418 and the pin could be in the lower cuff 18. Other arrangements for sliding between the lower cuff 18 and inner lower cuff 418 will be apparent to those skilled in the art such as guide tracks or other suitable arrangements.

What is claimed is:

1. A method of bracing a limb, having an upper portion, a lower portion and a joint between the upper and lower portion, comprising attaching a brace to the limb, the brace having a lower attachment for attachment to the lower portion of the limb and an upper attachment for attachment to the upper portion of the limb, a first lower strut attached to the lower attachment and extending along the lower portion of the limb toward the joint, a first upper strut attached to the upper attachment and extending along the upper portion of the limb toward the joint, and a first connecting mechanism to pivotally connect the first upper and first lower struts, the connecting mechanism having a lower telescoping portion slidably attached to the end of the first lower strut that is toward the joint, whereby the first lower strut slides out of the lower telescoping portion and away from the joint as the joint bends, and the connecting mechanism further having an upper telescoping portion slidably attached to the end of the first upper strut that is toward the joint, whereby the upper strut slides out of the telescoping portion and away from the joint as the joint bends.

2. The method of claim 1, wherein the upper and lower telescoping portions are pivotally connected to one another so that the upper and lower telescoping portions can pivot relative to one another to define an angle less than 180°, and the upper end of the first lower strut is connected to the upper telescoping portion by a first lower strut linkage arm having one end pivotally attached to the upper end of the first lower strut and another end pivotally attached to the upper telescoping portion at a location on the upper telescoping portion inside said angle such that the bending of the joint causes the first lower strut linkage arm to urge the first lower strut out of the lower telescoping portion.

3. The method of claim 2, wherein the lower end of the first upper strut is connected to the lower telescoping portion by a first upper strut linkage arm having one end pivotally attached to the lower end of the first upper strut and another end pivotally attached to the lower telescoping portion inside said angle such that the bending of the joint causes the first upper strut linkage arm to urge the first upper strut out of the upper telescoping portion.

4. A method of bracing a limb, having an upper portion, a lower portion and a joint between the upper and lower portion, comprising attaching a brace to the limb, the brace having a lower attachment for attachment to the lower portion of the limb and an upper attachment for attachment to the upper portion of the limb, a first lower strut attached to the lower attachment and extending along the lower portion of the limb toward the joint, a first upper strut attached to the upper attachment and extending along the upper portion of the limb toward the joint, and a first connecting mechanism to pivotally connect the first upper and first lower struts, the connecting mechanism having a lower telescoping portion slidably attached to the end of the first lower strut that is toward the joint, whereby the first lower strut slides out of the lower telescoping portion and away from the joint as the joint bends, and the connecting mechanism further having an upper telescoping portion slidably attached to the end of the first upper strut that is toward the joint, whereby the upper strut slides out of the telescoping portion and away from the joint as the joint bends and further comprising a second lower strut attached to the lower limb attachment and extending along the lower portion of the limb toward the joint, a second upper strut attached to the upper limb attachment and extending along the upper portion of the limb toward the joint, and a second connecting mechanism to pivotally connect the second upper and second lower struts; the second upper strut, second lower strut and second connecting mechanism being located such that they are on the opposite side of the limb from the first upper strut, first lower strut and first connecting mechanism when the apparatus is attached to a limb.

5. The method of claim 4, wherein the second connecting mechanism allows universal pivoting of the second upper and second lower struts.

6. The method of claim 5, wherein the second connecting mechanism includes a socket attached to one of the upper end of the second lower strut and the lower end of the second upper strut and a ball seated in said socket and attached to the other of the upper end of the second lower strut and the lower end of the second upper strut.

7. The method of claim 6, wherein the socket includes a ball seat and a cap attached to the ball seat, the ball seat and the cap enclosing a void to receive the ball, the cap having an opening therethrough for one of the upper end of the second lower strut and the lower end of the second upper strut to extend, the opening being oval-shaped to allow a greater degree of play of the strut in a first direction than in a second direction substantially perpendicular to the first direction, the first direction being in a plane substantially parallel to the plane containing the second struts and the second direction being in a plane substantially perpendicular to the plane containing the second struts.

8. The method of claim 4, wherein the first lower strut, first upper strut and first connecting mechanism are constructed for positioning on the side of the limb closest to the center of the body and the second lower strut, second upper strut and second connecting mechanism are constructed for positioning on the side of the limb furthest from the center of the body.

9. The method of claim 4, wherein the connecting mechanism includes a first lower telescoping portion slidably attached to the end of the first lower strut that is toward the joint, a second lower telescoping portion slidably attached to the end of the second lower strut that is toward the joint, a first upper telescoping portion slidably attached to the end of the first upper strut that is toward the joint, and a second strut slidably attached to the end of the second upper telescoping portion that is toward the joint, the first upper and first lower telescoping portions being pivotally connected to one another, and the second upper and second lower telescoping portions being pivotally attached to one another.

10. The apparatus of claim 9, wherein one of the upper and lower limb attachments includes a cuff attachable to the limb, and a cuff mount attached to one of the first and second upper struts and the first and second lower struts, the cuff mount and the cuff being attached to one another to accommodate rotation of the limb to which the cuff is attached about the limb's longitudinal axis as the joint bends or unbends.

11. The apparatus of claim 10, wherein one of the cuff and cuff mount has a slot in a direction substantially perpendicular to the limb longitudinal axis and the other of the cuff and cuff mount has a pin slidably mounted in the slot so that as the cuff rotates in relation to the cuff mount the pin slides through the slot.

* * * * *